United States Patent [19]
Darougar et al.

[11] Patent Number: 5,322,691
[45] Date of Patent: Jun. 21, 1994

[54] OCULAR INSERT WITH ANCHORING PROTRUSIONS

[76] Inventors: Sohrab Darougar, 2 Digby Pl., Croydon CR0 5QR, England; Alan L. Weiner, 28 Priory Rd., Cranburry, N.J. 08512

[21] Appl. No.: 83,303

[22] Filed: Jun. 29, 1993

Related U.S. Application Data

[60] Continuation-in-part of Ser. No. 944,438, Sep. 14, 1992, abandoned, which is a division of Ser. No. 626,001, Dec. 12, 1990, Pat. No. 5,147,647, which is a continuation-in-part of Ser. No. 500,093, Mar. 21, 1990, abandoned, which is a continuation of Ser. No. 330,959, Mar. 29, 1989, abandoned, which is a continuation of Ser. No. 104,045, Oct. 1, 1987, abandoned.

[30] Foreign Application Priority Data

Oct. 2, 1986 [GB] United Kingdom ............... 8623661
Dec. 11, 1990 [GB] United Kingdom ............... 9026888

[51] Int. Cl.$^5$ ............................................. A61F 9/00
[52] U.S. Cl. ................................. 424/427; 424/428; 424/429
[58] Field of Search ..................... 424/427, 428, 429

[56] References Cited

U.S. PATENT DOCUMENTS

| | | | |
|---|---|---|---|
| 3,828,777 | 8/1974 | Ness | 424/427 |
| 3,995,635 | 12/1976 | Higuchi et al. | 424/427 |
| 4,014,335 | 3/1977 | Arnold | 424/427 |
| 4,034,758 | 7/1977 | Theeuwes | 424/427 |
| 4,135,514 | 1/1979 | Zaffaroni et al. | 424/427 |
| 4,164,559 | 8/1979 | Miyata et al. | 424/428 |
| 4,524,776 | 6/1985 | Withers et al. | 424/427 |
| 5,164,188 | 11/1992 | Wong | 424/427 |
| 5,229,128 | 7/1993 | Haddad et al. | 424/427 |

OTHER PUBLICATIONS

Miguel F. Refojo, Ophthalmic Hydrogels, *Synthetic Biomedical Polymers, Concepts and Applications*, 1980, pp. 171–185.

Primary Examiner—Thurman K. Page
Assistant Examiner—Amy L. Hulina
Attorney, Agent, or Firm—Nies, Kurz, Bergert & Tamburro

[57] ABSTRACT

A flexible ocular insert device adapted for the controlled sustained release of an ophthalmic drug into the eye. In one embodiment, the device includes an elongated body of a polymeric material in the form of a rod or tube containing a pharmaceutically active ingredient and with at least two anchoring protrusions extending radially outwardly from the body. The device has a length of at least 8 mm and the diameter of its body portion including the protrusions does not exceed 1.9 mm. The sustained release mechanism may, for example, be by diffusion or by osmosis or bioerosion. The insert device is advantageously inserted into the upper or lower fornix of the eye so as to be independent of movement of the eye by virtue of the fornix anatomy. The protrusions may be of various shapes such as, for example, ribs, screw threads, dimples or bumps, truncated cone-shaped segments or winding braid segments. In a further embodiment, the polymeric material for the body is selected as one which swells in a liquid environment. Thus a device of smaller initial size may be employed. The present insert device is of a size and configuration such that, upon insertion into the upper or lower fornix, the device remains out of the field of vision so as to be well retained in place and imperceptible by a patient over a prolonged period of use. The device can be retained in the upper or lower fornix for 7 to 14 days or longer.

25 Claims, 7 Drawing Sheets

OCULAR INSERT WITH ANCHORING PROTRUSIONS

BACKGROUND OF THE INVENTION

This is a continuation-in-part of application Ser. No. 944,438 filed Sep. 14, 1992 now abandoned, which is a division of application Ser. No. 626,001 filed Dec. 12, 1990, now U.S. Pat. No. 5,147,647, which is a continuation-in-part of application Ser. No 500,093 filed Mar. 21, 1990 now abandoned, which is a continuation of application Ser. No. 330,959 filed Mar. 29, 1989 now abandoned which is a continuation of application Ser. No. 104,045 filed Oct. 1, 1987 now abandoned.

This invention is concerned with improvements in or relating to ocular insert devices.

Various diseases of the eye are commonly treated by frequent daily application of ophthalmic drugs for example in the form of eye drops or ointment. While this is suitable and convenient in some cases, it can be a serious disadvantage that the drug is not present in the eye in a continuous manner. With a view to overcoming this disadvantage it has been previously proposed, for example, in U.S. Pat. No. 3,416,530 of R.A. Ness assigned to Alza Corporation and subsequent patents of Alza Corporation to provide a flexible ocular insert device adapted for the controlled sustained release of the drug.

In for example U.S. Pat. No. 3,828,777 of R.A. Ness assigned to Alza Corporation it is stated that the ocular insert can be fabricated in any convenient shape for comfortable retention in the conjunctival sac of the eye and that the marginal outline can be ellipsoid, doughnut-shape, bean-shape, banana-shape, circular or rectangular; and in cross section it can be doubly convex, concavoconvex, or rectangular. It is suggested however that the original cross-sectional shape of the device is not of controlling importance. However, these previously proposed devices have in practice met with no more than limited success because most of the proposed shapes and sizes were not suitable for placement in the narrow upper and lower fornices. Also previous devices have tended not to remain in place in the eye and have at times caused irritation to the patient during use.

U.S. Pat. No. 4,186,184 to A. Zaffaroni discloses that the length of an insert device should be from 2 to 20 mm, its width 1 to 15 mm and its thickness 0.1 to 4 mm. A wide variety of shapes are disclosed, including ellipsoid, doughnut, bean, banana and square shapes.

U.S. Pat. No. 3,828,777 to Ness discloses an ocular device which is inserted in that portion of the eye bounded by the surfaces of the bulbar conjunctiva of the sclera of the eyeball and the palpebral conjunctiva of the lid. Such placement of the device would, however, be subject to eye movement and would not provide an anchored position such as is obtained in the present invention. Movement of the device causes pain, irritation, foreign body sensation and watering.

U.S. Pat. No. 4,343,787 to Katz discloses water soluble inserts for the eye in which broad dimensional ranges of sizes and shapes are employed. There is no description of an insert of a specific size and shape to allow it to be retained in the fornix portion of the eye.

U.S. Pat. No. 4,135,514 to Zaffaroni et al. relates to osmotic drug delivery devices which can be used for the administration of ocular drugs. A wide variety of shapes and sizes is disclosed.

EP-A-0 033 042 to Merck and Co., Inc. discloses ocular inserts which can take any of a variety of shapes, one of which may be an extruded rod. There is no description, however, of a device having dimensions which make it suitable for insertion into the fornix so as to be retained therein for 7 days or longer.

U.S. Pat. No. 4,730,013 to Bondi et al. discloses ocular inserts intended to overcome the problem of blurred vision arising from the use of particular insert materials. The maximum length of 5 mm employed by Bondi et al. is considerably smaller than the range of dimensions employed in the present invention. It is shown in the present invention that a device with a length of 5 mm falls well below the minimum length required for retention in the eye of humans for 7 days or more.

EPO 0 251 680 to IOLAB, Inc. discloses a device for controlled drug release to the eye, in which an external matrix rapidly soluble in body fluids and having bioerodible microparticles containing the drug are positioned in the upper or lower conjunctival cul-de-sac of the eye. There is no description of a device which is retained in the eye for seven days or longer, or of the specific shape and dimension of the device of the invention for placement in the upper or lower fornix.

U.S. Pat. No. 3,845,201 to Haddad et al. discloses an ocular device for insertion in the cul-de-sac of the conjunctiva. The device may be any of various shapes, preferably disc shaped.

U.S. Pat. No. 4,164,559 to Miyata et al. discloses a soluble device for drug delivery to the eye including a collagen insert having an ovoid shape. The device is described as insertable into the inferior fornix. There is no description of a device having the dimensions employed in the present invention for retention of seven days or longer.

U.S. Pat. No. 4,179,497 to Cohen et al. discloses water soluble inserts of various shapes for applying drugs to the cul-de-sac of the conjunctiva. Again there is no description of an insert having the specific dimensions of the invention In the use of a prior art device known as Ocusert, the subject of U.S. Pat. No. 3,828,777 to Ness, the device is inserted into the conjunctival cul-de-sac. Either of two systems may be employed, with the Pilo-20 system measuring 5.7×13.4 mm on its axes and 0.3 mm in thickness and the Pilo-40 system measuring 5.5×13 mm on its axes and 0.5 mm in thickness. Various problems in retention and irritation which occurred in the use of this device are documented, for example, in the following publications: P. Sihvola et al., Practical problems in the use of Ocusert-pilocarpine delivery system, *Acta Ophthalmol.(Copenh.)*, December 1980, 58 (6),pp 933-937; S.E. Smith et al., Comparison of the pupillary, refractive and hypotensive effects of Ocusert-40 and pilocarpine eyedrops in the treatment of chronic simple glaucoma, Br. J. Ophthalmol., April 1979, 63(4) pp 228-232; and I.P. Pollack et al., The Ocusert pilocarpine system: advantages and disadvantages, *South Med. J.*, October 1976, 69 (10), pp 1296-1298.

Other ocular inserts are described in the following literature reports: Urtti et al. (1990) Controlled drug delivery devices for experimental ocular studies with timolol.1. In vitro release studies. *Int. J, Pharm.*, 61, 235-240; and Urtti et al (1990) Controlled drug delivery devices for experimental ocular studies with timolol.-2.Ocular and systemic absorption in rabbits. *Int. J. Pharm.*, 61, 241-249. These reports describe the use of a permeable hollow tube (silicone) for ocular delivery.

The tube has a diameter of 1.94 mm which is outside the dimensions employed in the present invention. Also, the device was only observed in the eye for an 8 hour period.

SUMMARY OF THE INVENTION

It is an object of the present invention to provide an improved ocular insert device adapted for the controlled sustained release of a drug. The present invention is sometimes referred to herein as OCUFIT SR.

It has been found, in accordance with the present invention, that a flexible ocular insert device having a body of a thin elongated circular cylindrical configuration of specific dimensions and with anchoring protrusions of specific dimensions is well retained in place and tolerated by the patient over a prolonged period of use, for example, up to 7 to 14 days or longer. The device may be inserted in the upper or lower fornix of the conjunctiva between the sclera of the eyeball and the upper or lower eyelid, being held in position preferably in the extreme outer end portion of the upper or lower fornix and prevented from moving downward or upward respectively by the pressure of the lid against the eyeball. This position of the ocular insert of the present invention in the upper or lower fornix is shown in detail in the drawings as described hereinafter.

In particular, the device is advantageously inserted so as to fit within the upper or lower fornix by restriction of the cross sectional dimensions of the device to allow it to slip into this position and then with a length requirement that provides for anchoring the device across the lid. Two or more protrusion elements extend radially outwardly from the core to minimize lateral movement when the device is positioned within the fornix. By locating the device within the fornix, the device is imperceptible to the patient, through restriction of the device to a specific size range and shape, with the upper limit not being governed by the geometric space limitation of the whole eye, and by placement specifically within the fornix, not simply within the conjunctival cul-de-sac. In addition, the retention of the present insert device is independent of the movement of the eye by virtue of the fornix anatomy. In contrast, a device placed anywhere on the bulbar conjunctiva would be subject to eye movement and cause discomfort to the patient.

The insert device of the present invention must be positioned precisely and remain anchored in the upper or lower fornix, known also as the superior conjunctival fornix or the inferior conjunctival fornix, as distinct from the positioning of other kinds of devices anywhere in the conjunctival cul-de-sac. The device of the present invention must be flexible to allow it to bend along the curvature of the eye within the fornix. In particular, such flexibility must be sufficient to allow it to bend along the curvature of the eye within the upper or lower fornix upon being positioned so that the longitudinal axis of the device is generally parallel to the transverse diameter of the eyeball.

The present insert device is imperceptible by the patient when anchored properly in the fornix, whereas prior art devices are perceived as foreign bodies. Upon proper positioning in the fornix, the present insert device is independent of eye movement and does not move when the eye moves. The device of the present invention also remains out of the field of vision. In addition, it can be placed and held in position without interference during surgical procedures.

The length of the present insert device is also critical to the anchoring process in the fornix. The length of the device is related to the size of the eye, hence the optimum length for the human adult is 25 mm, for children is about 15 to 18 mm and for newborn babies is 8 mm in length.

In general, for adults, the lengths of the upper fornix and lower fornix are about 45 to 50 mm and 35 to 40 mm respectively. Thus an insert device of the present invention with a length of up to 35 mm may remain in the upper fornix and one with a length of up to 25 mm may remain in the lower fornix without causing discomfort.

The invention provides, in one of its aspects, a flexible ocular insert device adapted for the controlled sustained release of an ophthalmic drug into the eye, characterized in that the device comprises a body having a thin elongated circular cylindrical configuration with at least two radially outwardly extending protrusions, the device having a length of at least 8 mm and a diameter including the protrusions not exceeding 1.9 mm. Advantageously the dimensions of the device according to the invention are selected as: a length of 8 to 25 mm for use in the lower fornix and a length of 8 to 35 mm for use in the upper fornix; and a diameter of 0.5 to 1.9 mm.

The circular cylindrical body terminates at transverse end surfaces which may for example be planar or domed.

The material of the insert device is for example a synthetic polymer.

The present invention provides a flexible ocular insert device adapted for the controlled sustained release of an ophthalmic drug into the eye, characterized in that the device comprises a body having a circular, cylindrical configuration; the length of the device is at least 8 mm and the diameter of its body including protrusions does not exceed 1.9 mm. A plurality of protrusion elements extend radially outwardly from the body, with the protrusion elements being arranged in various patterns such as ribs or a screw configuration. The protrusions should extend radially outwardly a distance sufficient to allow the device to become anchored in the fornix tissue. Generally, the protrusions will extend outwardly a distance such that the overall diameter of the device including the protrusions is approximately 15 to 30 percent greater than the diameter of the body or core.

Examples of ophthalmic drugs include antibiotics such as tetracycline, chlortetracycline, bacitracin, neomycin, polymyxin, gramicidin, cephalexin, oxytetracycline, chloramphenicol, kanamycin, rifampicin, tobramycin, gentamicin, erythromycin and penicillin; antibacterials such as sulfonamides, sulfadiazine, sulfacetamide, sulfamethizole and sulfisoxazole, nitrofurazone and sodium propionate; antivirals including idoxuridine, trifluorothymidine, acyclovir, ganciclovir and interferon; antiallergenics such as sodium cromoglycate, antazoline, methapyriline, chlorpheniramine, cetirizine and prophenpyridadine; antiinflammatories such as hydrocortisone, hydrocortisone acetate, dexamethasone, dexamethasone 21-phosphate, fluocinolone, medrysone, prednisolone acetate, fluoromethalone, betamethasone, and triamcinolone and non-steroidal agents such as indomethacin, diclofenac, flurbiprofen, piroxicam, ibuprofen and acetyl salicylic acid; decongestants such as phenylephrine, naphazoline and tetrahydrozoline: miotics and anticholinesterase such as pilocarpine, acetylcholine chloride, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immune stimulants; hormonal agents such as estrogens, estradiol, progestational, progesterone, insulin, calcitonin, parathyroid hormone and peptide, vasopressin, hypothalamus releasing factor; beta adrenergic blockers such as timolol maleate, levobunolol HC1 and betaxolol HC1; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors.

The drugs may be used in conjunction with a pharmaceutically acceptable carrier. Examples of pharmaceutically acceptable carriers include solids such as starch, gelatin, sugars, e.g., glucose, natural gums, e.g., acacia, sodium alginate, carboxymethyl cellulose, polymers, e.g., silicone rubber; liquids such as sterile water, saline, dextrose, dextrose in water or saline; condensation products of castor oil and ethylene oxide liquid glyceryl triester of a lower molecular weight fatty acid; lower alkanols; oils such as corn oil, peanut oil, sesame oil, and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxy-methylcellulose, sodium alginate, poly(vinylpyrolidone), alone, or with suitable dispensing agents such as lecithin, polyoxyethylene stearate. The carrier may also contain adjuvants such as preserving, stabilizing, wetting or emulsifying agents.

The mechanism of controlled sustained drug release into the eye is for example diffusion, osmosis or bio-erosion and these mechanisms are described for example in U.S. Pat. No. 4,186,184 and in "Therapeutic Systems" by Klaus Heilmann published by Georg Thieme, Stuttgart 1978.

The period of controlled sustained release is for example up to 7 to 14 days or longer.

In one exemplary embodiment of the present invention utilizing the diffusion mechanism, the configuration of the body of the insert device is tubular with its cylindrical wall closed by transverse end walls to define a reservoir for the drug which is in liquid or gel form. At least the cylindrical wall is a membrane permeable by diffusion so that the drug is released continuously at a controlled rate through the membrane into the tear fluid.

In one exemplary embodiment of the invention utilizing the osmosis mechanism, the configuration of the body of the insert device is tubular with domed end walls, and the device comprises a transverse impermeable elastic membrane dividing the tubular interior of the device into a first compartment and a second compartment; the first compartment is bounded by a semipermeable membrane and the impermeable elastic membrane, and the second compartment is bounded by an impermeable material and the elastic membrane. There is a drug release aperture in the impermeable end wall of the device.

The first compartment contains a solute which cannot pass through the semi-permeable membrane and the second compartment provides a reservoir for the drug which again is in liquid or gel form.

When the device is placed in the aqueous environment of the eye water diffuses into the first compartment and stretches the elastic membrane to expand the first compartment and contract the second compartment so that the drug is forced through the drug release aperture.

In one exemplary embodiment of the invention utilizing the bioerosion mechanism, the configuration of the body of the insert device is rod-like being constituted from a matrix of bioerodible material in which the drug is dispersed. Contact of the device with tear fluid results in controlled sustained release of the drug by bioerosion of the matrix. The drug may be dispersed uniformly throughout the matrix but it is believed a more controlled release is obtained if the drug is superficially concentrated in the matrix.

In another embodiment of the invention, there is employed a solid non-erodible rod with pores and dispersed drug. The release of drug can take place via diffusion through the pores. Controlled release can be further regulated by gradual dissolution of solid dispersed drug within this matrix as a result of inward diffusion of aqueous solutions.

Examples of the materials for a permeable membrane for the diffusion mechanism include but are not limited to insoluble microporous materials of polycarbonates, polyvinyl chlorides, polyamides, copolymers of polyvinyl chloride and acrylonitrile, polyethylene, polypropylene, polysulphones, polyvinylidene fluorides, polyvinyl fluorides, polychloroethers, polyformaldehydes, acrylic resins, polyurethanes, polyimides, polybenzimadozoles, polyvinyl acetates, polyethers, cellulose esters, porous rubbers, cross-linked poly (ethylene oxide), crosslinked polyvinyl pyrrolidone, cross-linked poly (vinyl alcohol) and polystyrenes.

The drug in liquid or gel form for the diffusion mechanism comprises a diffusion medium which also serves as a pharmaceutical carrier and in which the active ingredient of the drug is dissolved or suspended; the active ingredient is preferably of no more than limited solubility in the medium. Examples of diffusion media include saline, glycerin, ethylene glycol, propylene glycol, water (which may also contain emulsifying and suspending agents), mixtures of propylene glycol monostearate and oils, gum tragacanth, sodium alginate, poly(vinyl pyrrolidone), polyoxyethylene stearate, fatty acids and silicone oil.

Examples of materials for an osmotic semi-permeable membrane include but are not limited to cellulose acetate and its derivatives, partial and completely hydrolyzed ethylene-vinyl acetate copolymers, highly plasticized polyvinyl chloride, homo and copolymers of polyvinyl acetate, polyesters of acrylic acid and methacrylic acid, polyvinyl alkyl ethers, polyvinyl fluoride; silicone polycarbonates, aromatic nitrogen-containing polymeric membranes, polymeric epoxides, copolymers of an alkylene oxide and alkyl glycidyl ether, polyurethanes, polyglycolic or polyacetic acid and derivatives thereof, derivatives of polystyrene such as poly(sodium styrenesulfonate) and poly(vinyl benzyltrimethylammonium chloride), ethylene-vinyl acetate copolymers.

Examples of solutes which cannot pass through the semipermeable membrane in an osmotic mechanism include but are not limited to water-soluble inorganic and organic salts and compounds such as magnesium sulfate, magnesium chloride, sodium chloride, lithium chloride, potassium sulfate, sodium carbonate, sodium sulfate, lithium sulfate, calcium bicarbonate, sodium sulfate, calcium sulfate, potassium acid phosphate, calcium lactate, magnesium succinate, tartaric acid, acetamide, choline chloride, soluble carbohydrates such as sorbitol, mannitol, raffinose, glucose, sucrose and lactose.

Examples of bioerodible matrix materials include but are not limited to polyesters of the general formula —O—(W)—CO— and mixtures thereof, wherein W is a lower alkylene of 1 to 7 carbons and may include a member selected from the group of alkylenes of the formula —CH$_2$—, or —CH—CH$_2$—, and Y has a value such that the molecular weight of the polymer is from about 4,000 to 100,000. The polymers are polymerizationcondensation products of monobasic hydroxy acid of the formula $C_nH_{2n}(OH)$ COOH wherein n has a value of 1 to 7, preferably 1 or 2 and the acid is especially lactic acid or glycolic acid. Also included are copolymers derived from mixtures of these acids. Bioerodible materials also include poly(orthoesters). These materials have the following general formula:

wherein $R_1$ is an alkylene of 4 to 12 carbons, a cycloalkylene of 5 to 6 carbons substituted with an alkylene of 1 to 7 carbons and an alkyleneoxy of 1 to 7 carbons, and $R_s$ is a lower alkyl of 1 to 7 carbons.

Other bioerodible matrix materials which may be employed include but are not limited to the following: (1) Polyanhydrides such as poly(p-carboxyphenoxy) alkyl (e.g. p-carboxyphenoxypropane) or polymeric fatty acid dimer (e.g. poly-dodecanedioic acid) compounds and further co-polymers with sebacic acid, or phthalic acid such as disclosed in Chasin et al., Polyanhdrides for Controlled Drug Delivery, *Biopharm.*, February 1988, 33–46; and Lee et al. (1988), The Use of Bioerodible Polymers and 5 fluorouracil in Glaucoma Filtration Surgery, *Invest. Ophthalmol. Vis. Sci.*, 29, 1692–1697; (2) Poly (alkyl-2-cyanoacrylates) such as poly (hexyl-2-cyanoacrylate) as described by Douglas et al. (1987), Nanoparticles in Drug Delivery, *CRC Crit. Rev. Therap. Drug Carr. Syst.*, 3, 233–261; and (3) Polyamino acids such as copolymers of leucine and methyl glutamate.

Further information on membrane and bioerodible materials is contained in U.S. Pat. Nos. 3,828,777 and 4,186,184 and also the following references: Leong and Langer (1987), Polymeric Controlled Drug Delivery, *Adv. Drug Del. Rev.*, 1, 199–233; and Smith et al. (1990), Bioerodible Polymers for Delivery of Macromolecules, *Adv. Drug Del. Rev.*, 4, 343–357.

Examples of materials for use as non-erodible rods include but are not limited to polymers such as hydroxyethylmethacrylate and further co-polymers with methacrylic acid, methylmethacrylate, N-vinyl 2-pyrrolidone, allyl methacrylate, ethylene glycol dimethacrylate, ethylene dimethacrylate, or 1,1,1 trimethylopropane trimethacrylate, and dimethyl diphenyl methylvinyl polysiloxane.

The above and other aspects of the present invention will become more clear from the following description, to be read with reference to the accompanying drawings of devices embodying the invention. This description is given by way of example only, and not by the way of limitation of the invention.

DESCRIPTION OF THE PREFERRED EMBODIMENTS

Figure 1:
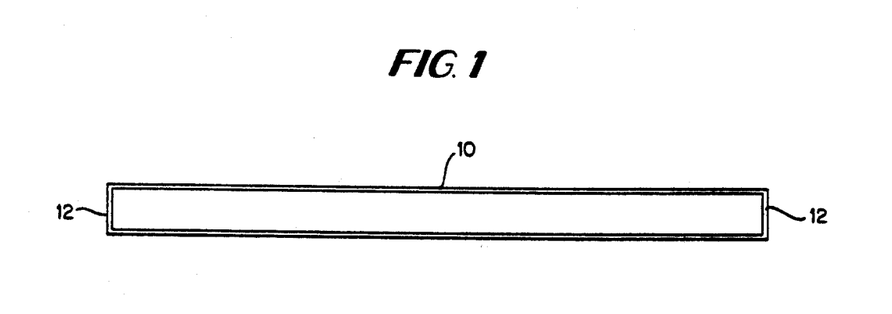
FIG. 1 shows a diagrammatic sectional view of a diffusional ocular insert device embodying the invention.

The ocular insert device shown in FIG. 1 comprises a circular cylindrical wall 10 of a microporous synthetic polymer membrane which is insoluble in tear fluid but is permeable by diffusion. The cylindrical wall 10 is closed by transverse planar end walls 12 which may be of the same microporous synthetic polymer membrane as the cylindrical wall 10 or alternatively may be impermeable. The overall length of the device is 8 to 25 mm or up to 35 mm for the upper fornix and its external diameter 0.5–1.9 mm.

The cylindrical wall 10 and the end walls 12 define a reservoir for a drug which diffuses through the membrane as described hereinbefore.

Figure 2:
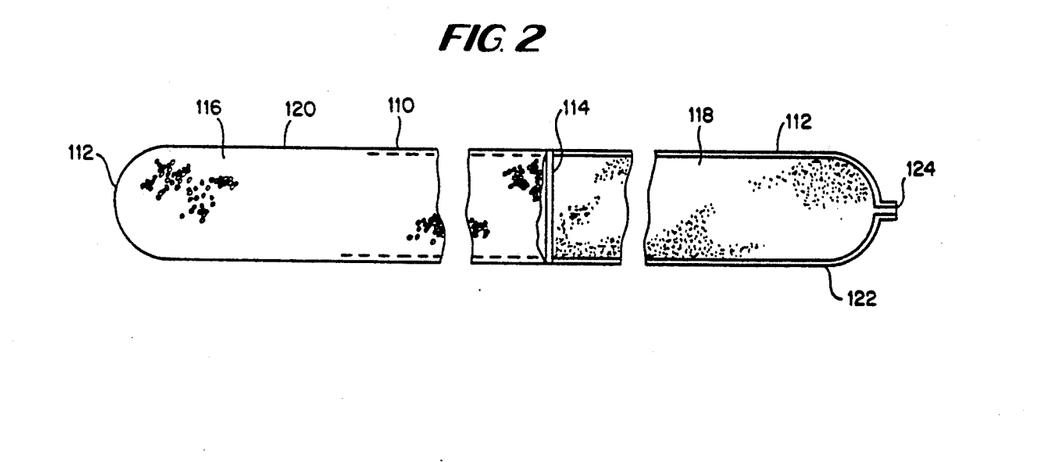
FIG. 2 shows a diagrammatic sectional view of an osmotic ocular insert device embodying the invention.

The ocular insert device shown in FIG. 2 comprises a circular cylindrical wall 110 closed by hemispherical domed end portions 112. The device also comprises, perpendicular to the axis of the cylindrical wall, an impermeable elastic membrane 114 dividing the interior of the device into a first compartment 116 and a second compartment 118. The cylindrical wall 110 comprises different materials as respectively do the end walls 112 so that the first compartment is bounded by a semipermeable synthetic poller membrane 120 and the elastic membrane 114 and the second compartment is bounded by an impermeable synthetic polymeric membrane 122 and the elastic membrane 114. There is an axial drug release aperture 124 in the membrane 122 at the domed end portion 112 thereof.

The first compartment 116 contains a solute and the second compartment provides a reservoir for a drug which is forced through the aperture 124 by the stretching of the elastic membrane 114 under osmosis as described hereinbefore.

Figure 3:
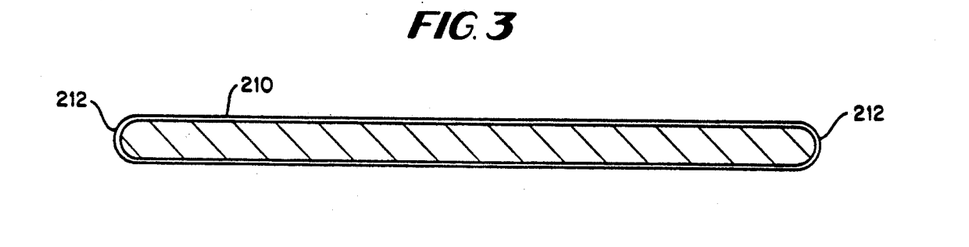
FIG. 3 shows an enlarged diagrammatic sectional view of a bioerodible insert device embodying the invention.

The ocular insert device shown in FIG. 3 comprises a circular cylindrical body 210 with domed end portions 212. The device is constituted from a matrix of synthetic polymeric bioerodible material in which a drug is dispersed, being concentrated superficially of the matrix for controlled release therefrom as the matrix bioerodes.

The device having the configuration as shown in FIG. 3 may also be constituted of a solid non-erodible material having pores and dispersed drug as previously discussed.

The overall length and diameter of each of the devices of FIG. 2 and FIG. 3 is the same as for the device of FIG. 1.

The ocular insert device of the present invention may be installed in the fornix by the method as follows. The applicator consists of a tube with a length of about 35 mm and a flexible container with a capacity of about 500 microliter containing a pharmaceutically acceptable viscous substance in the form of a cream:

(a) Insert the OCUFIT SR device into the tube. Squeeze the container until the viscous substance pushes the device into the mouth of the tube.

(b) Ask the patient to sit down and hold his/her chin slightly up.

(c) Ask the patient to look down continuously throughout the exercise.

(d) Separate the upper lid from the globe by about 4 to 5 mm by holding the lashes and gently pulling the lid forward and upward. Insert the tube under the eyelid for about 5 mm near the inner corner (nasal canthus) of the eye. Do not touch the inner corner of the eye and the globe.

(e) Push out the OCUFIT SR device by squeezing the container gently and continuously. In the meantime move the tube slowly from the inner corner (nasal canthus) toward the outer corner (temporal canthus), holding the tip of the tube at about 5 mm from the lid margin constantly. Stop about 5 mm from the outer corner.

N.B. By squeezing the container and moving the tube from one corner to another corner of the eye, the OCUFIT SR device should come out of the tube and sit between the lid and globe near the upper fornix.

(f) Put tip of a finger at just about the end of the tube and hold the end of the OCUFIT SR device in position. Remove the tube.

(g) With the help of the tip of a finger, gently push the OCUFIT SR device upward and toward the deep fornix. Repeat the movement twice more, once in the middle of the lid and once near the inner corner.

(h) Ask the patient to move the eye upward and downward three times. Make sure that the device is in position and is not coming out.

The device may also be installed directly by the patient using similar procedures as described above.

Figure 4:
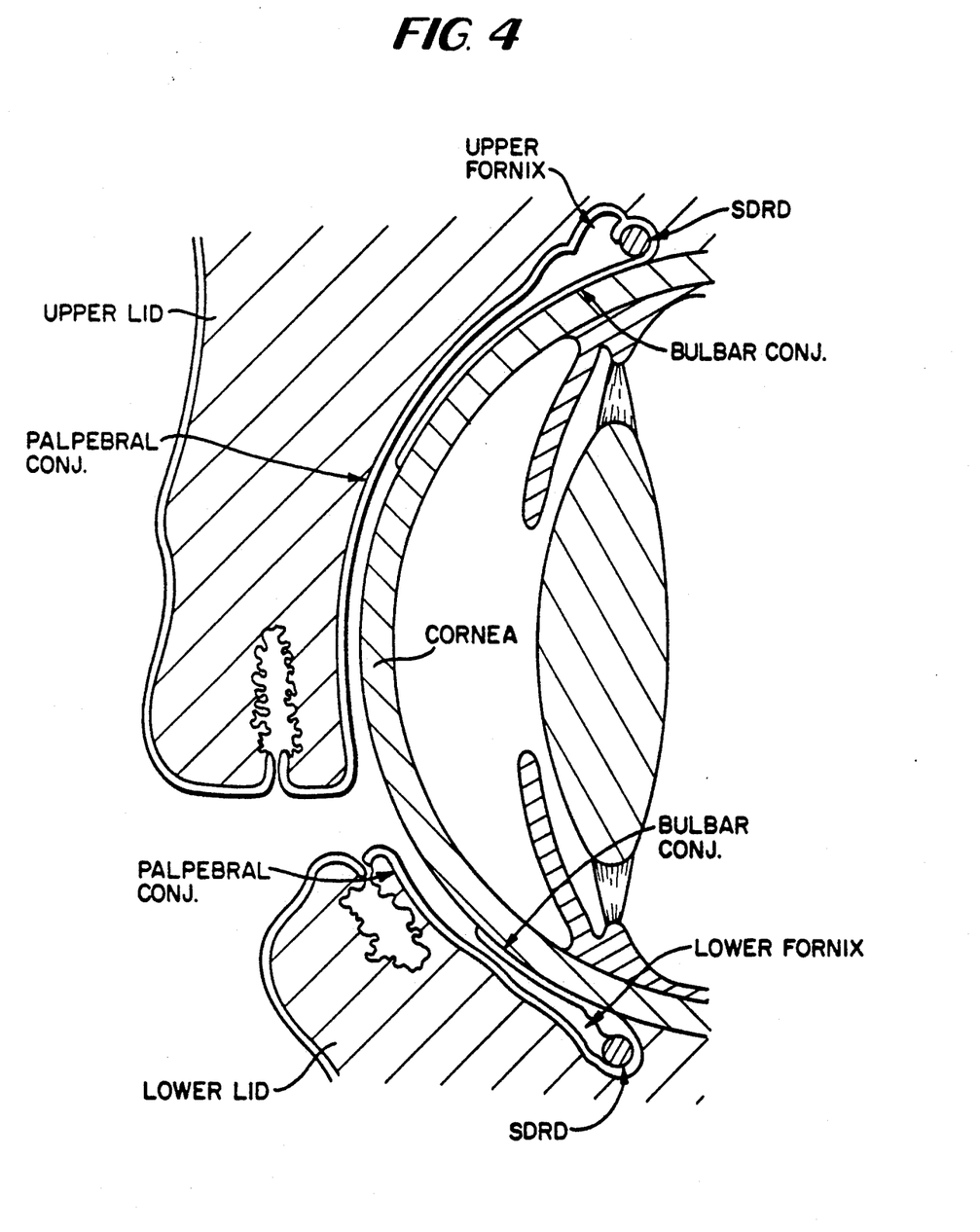
FIG. 4 shows a diagrammatic sectional view of the eye with an ocular insert device of the present invention installed in the upper and lower fornix.
Figure 5:
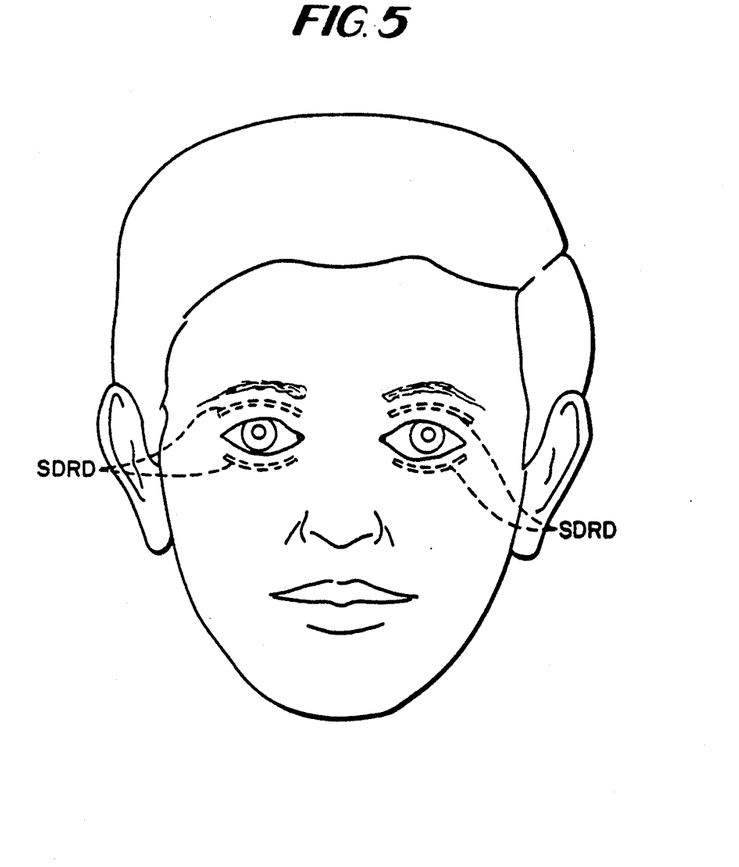
FIG. 5 shows a representation of the head of a patient with the location of the installed ocular insert device shown in dashed lines.
Figure 6:
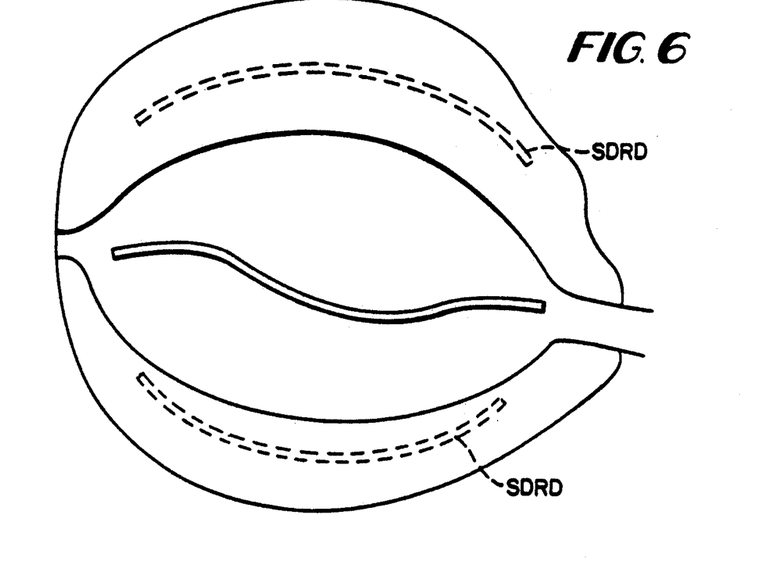
FIG. 6 shows the position of the installed ocular insert device in a closed eye.

Upon installation, the ocular insert device of the present invention will be positioned in the upper or lower fornix in one of the positions identified as SDRD as shown in FIGS. 4 through 6 of the drawings.

By the way of comparison, ocular inserts having dimensions outside those of the present invention were constructed, with dimensions as follows:

Size: Approximately 12×5×1 mm
Shape: Oval, Lower surface with concave curvature, upper surface with convex curvature
Composition: Polypeptide matrix containing erythromycin estolate
Consistency: Semi-rigid These inserts outside the scope of the present invention were placed in the upper fornix of the right eye of 16 patients between the ages of 6 and 8. The retention of the device in this location was followed over a period of 10 days. The right eye was examined twice a day for the presence of the insert. A new insert was replaced in the fornix if dislocation occurred. The results which were obtained showed that inserts of this type outside the scope of the present invention required frequent replacement into the eye over a ten day period. In no case were such inserts retained for more than 3 days at a time.

The foregoing comparative tests show the importance of employing an ocular insert device having the size and shape as described herein.

In further embodiments of the invention, as shown in FIGS. 7 through 12, the drug releasing device or OCUFIT SR device of the present invention may be formed with a central, longitudinally extending body or core portion, and with two or more protrusion elements extending radially outwardly from the core. The protrusion elements may be of various alternative shapes such as ribs or screw shapes so that the device may be, for example, of a ribbed design, a screw design, a bump design, a segmental design or a braided design. The protrusion elements function to anchor the device in the fornix, with the tissue of the fornix filling the spaces or interstices surrounding the device between protrusions.

At least two protrusions should be employed, with a view toward providing an overall symmetrical shape for the device. In a case where only two protrusions are employed, such protrusions should be evenly spaced relative to the length of the device so that the protrusions will be equidistant from their respective ends of the device. Where more than two protrusions are employed, it is important to provide a symmetrical arrangement with even spacing so as to achieve a uniform anchoring function along the length of the device.

Figure 7:
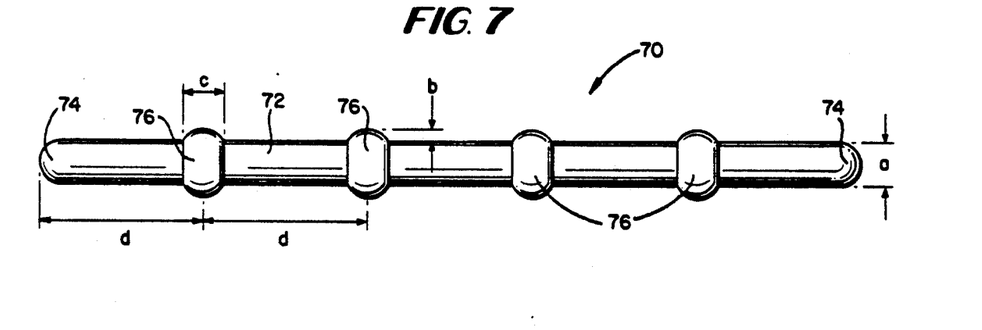
FIGS. 7 through 12 show diagrammatic views of further embodiments of the ocular insert device of the present invention, with various anchoring configurations.

As shown in FIG. 7, the device 70 with ribbed configuration has circular cylindrical walls 72 with domed end portions 74. A series of arcuate shaped ribs 76, of circular, toroidal cross section, are provided at intervals along the length of the device 70. In one embodiment, the device 70 had a core diameter "a" of 1.4 mm and with the ribs protruding outwardly from the core by a distance "b" of 0.15 mm. In this embodiment, the ribs 76 had a width "c" of 1 mm and an interval "d" between ribs 76 of 5 mm and the overall length of the device 70 was 25 mm.

In another embodiment similar to that of FIG. 7, a device 70 having a total of five ribs 76 was employed, with the space between ribs 76 being adjusted accordingly so that the ribs 76 were equally spaced apart. As few as two ribs may be employed, with one rib 76 being located adjacent each end portion of the device 70. In these embodiments as with those embodiments described hereinafter, the tissue of the fornix fills the spaces or interstices surrounding the device 70 between the protrusions, which in this case are the ribs 76.

Figure 8:
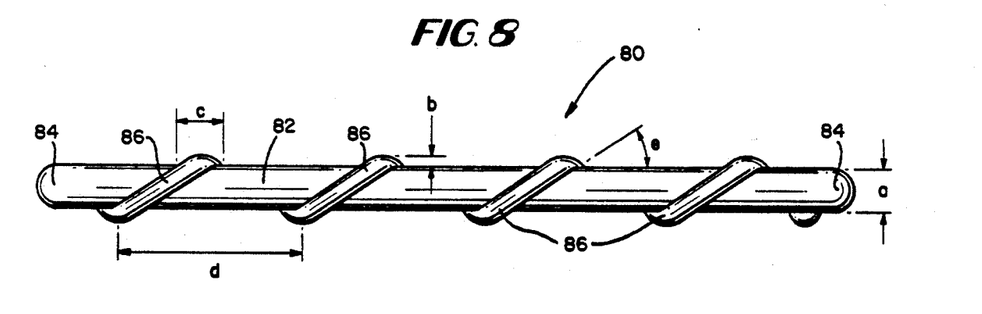

In FIG. 8 there is shown a device 80 with screw configuration having circular cylindrical walls 82 with domed end portions 84. A series of screw-type protrusions 86 are provided at intervals along the length of the device 80. In one embodiment, the device 80 had a core diameter "a" of 1.4 mm and with the screw protrusions 86 extending outwardly from the core by a distance "b" of 0.15 mm. In this embodiment, the screw protrusions 86 had a width "c" of 1 mm and an interval "d" between protrusions 86 of 5 mm and the overall length of the device 80 was 25 mm. The angle "e" was approximately 28.9 degrees in this embodiment.

Figure 9:
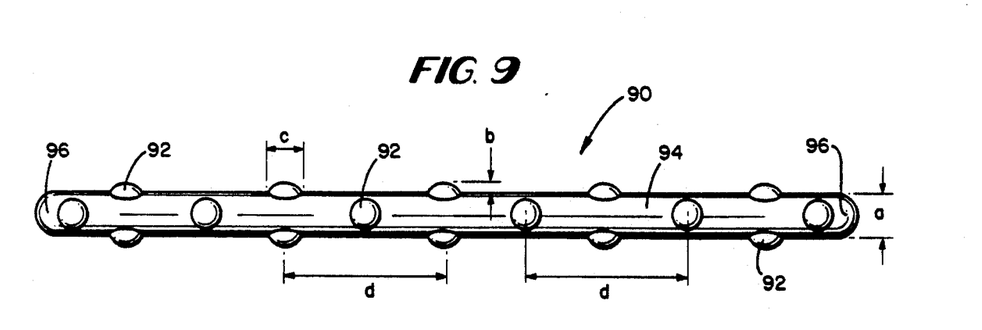

The device 90 of FIG. 9 has a plurality of raised dimples or bumps 92 having a generally hemispherical shape on the circular cylindrical walls 94 with domed end portions 96. In one embodiment, the device 90 had a core diameter "a" of 1.4 mm and with the bumps 92 extending outwardly from the core by a distance "b" of 0.15 mm. In this embodiment, the bumps 92 had a width "c" of 1 mm and an interval "d" between bumps 92 of 5 mm and the overall length of the device 90 was 25 mm. There were four longitudinally aligned rows of bumps 92 equally spaced about the circumference of the device 90 in this embodiment. The number of rows may vary from about 2 to 6.

Figure 10:
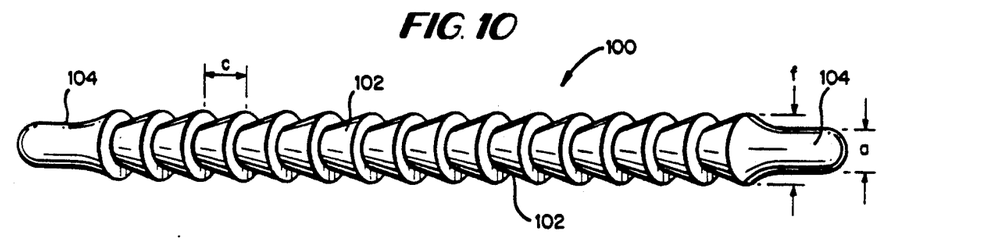

In FIG. 10 there is shown a device 100 with a segmental configuration having a series of truncated cone-shaped segments 102 interconnected along the length of the device 100 and with dome shaped end portions 104. In one embodiment, the device 100 had a core diameter "a" of 1.4 mm and with the length "c" of each segment 102 being about 1 mm. In this embodiment, the overall base width "f" of each segment 102 was 1.7 mm and the overall length of the device 100 was 25 mm.

Figure 11:
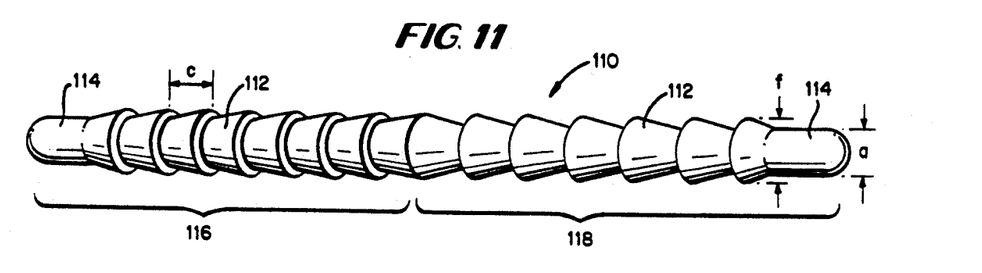

The device 110 of FIG. 11 also has a segmented configuration with a series of truncated cone-shaped segments 112 interconnected along the length of the device 110 and with dome-shaped end portions 114. In this embodiment, however, the device 110 is formed with mirror image segmental portions 116 and 118 so that the left one-half portion 116 of the device 110 is a mirror image of the right one-half portion 118. In one embodiment, the device 110 had a core diameter "a" of 1.4 mm and with the length "c" of each segment 112 being about 1 mm. In this embodiment, the overall base width "f" of each segment 112 was 1.7 mm and the overall length of the device 110 was 25

Figure 12:
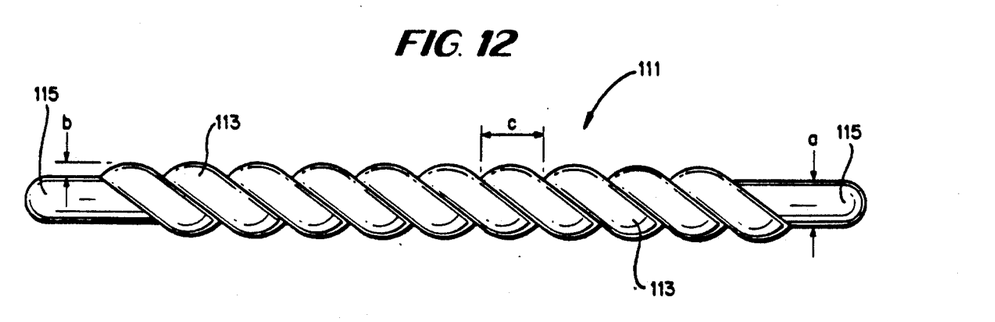

The device 111 of FIG. 12 has a braided design in which. a series of braided segments 113 are interconnected along the length of the device 111 and with dome shaped end portions 115. In one embodiment, the device 111 had a core diameter "a" of 1.4 mm and with the length "c" of each segment 113 being 1 mm. In this embodiment, the braided segments 113 extended outwardly from the core by a distance "b" of 0.15 mm and the overall length of the device 111 was 25 mm.

In a further embodiment of the invention, the ocular insert device of the present invention may be formed with a polygonal shape in cross section, with the polygon having, for example, five or six equal sides. Such polygonal shape may be employed as the central core with any of the configurations shown in FIGS. 7 through 12.

The drug loaded OCUFIT SR device can be formed by any of various processes such as extrusion molding, injection molding, transfer molding or compression molding.

In carrying out the extrusion molding process, polymer material is blended with drug at ratios of drug up to 40% by weight on a cooled two roll mill and then fed into a screw drive extruder. By the action of the single flight screw with diminishing pitch and a length to diameter ratio of about 12:1 to 10:1, material is continuously forced out through a coin or plate die (port) with openings conforming to the shape and dimensions of the subject device (i.e. circular). For designs involving tube configurations, a mandrel held in place by a spider flange is positioned prior to the die. The continuous noodle is pulled via conveyer belt through a heated horizontal or vertical chamber (315 to 425 degrees C.) to achieve vulcanization of the material. The final OCUFIT SR device is made by a cutting apparatus where the rods are cut to size. Additional modifications such as polishing the ends of the device can be accomplished.

In carrying out the transfer molding process, the blend of polymer material and drug is placed into a heated transfer press with an aluminum or stainless steel mold containing impressions of the proper shape and size. The material is forced into the mold..at between 200 and 4000 psi. The mold itself is kept under 10 tons of clamp pressure. The mold is kept heated and under pressure at any of the following conditions:

| | |
|---|---|
| 4–10 minutes | 135 degrees C. |
| 15 minutes | 100 degrees C. |
| 30 minutes | 75 degrees C. |
| 2 hours | 55 degrees C. |
| 5 hours | 40 degrees C. |
| 24 hours | Ambient temperature (25° C.) |

The mold is cooled, separated and the formed OCUFIT SR devices .are then removed.

In one embodiment, silicone rubbers/elastomers are employed as the material from which the device is formed. The silicone rubbers/elastomers are prepared as follows:

Silicone rubber prepared using dimethylsiloxane polymer or dimethyl and methylvinyl siloxane copolymers, reinforcing silica, platinum catalyst, inhibitor and siloxane crosslinker and other vulcanizing agents such as organic peroxides is either hand mixed, mixed on a two roll mill, or injection molded together with micronized drug (predominantly 10 micron particles or less). Drug is loaded into the polymer mixture at levels up to 40 weight percent of the total weight together with any other necessary excipients or release modifiers such as glycerin or sorbitol. Entrapped air within the mixture is removed by exposure to a vacuum of about 28 inches of mercury for approximately 30 minutes. Drug is solidified within the polymer matrix by curing (vulcanizing) the mixture while being molded into the desired shape.

The device may also be formed of bioerodible polymers prepared as follows:

Solid mixtures of bioerodible polymers (Polyhydroxyacids such as polylactic acid and polyglycolic acid, and polyhydroxybutyrate; Polyesters and polyorthoesters including cyclic ortho-esters with diols or diketeneacetals or diacids with diols or polyols; Polyanhydrides made from one or more of the following: p-carboxyphenoxy propane, p-carboxyphenoxy hexane, sebacic acid, dodecanedioic acid, 1,4-phenylenedipropionic acid, isophthalic acid, polypropylene fumarate and polypropylene maleate; Polypeptides; and Polycyanoacrylates) can be admixed with up to about 60% by weight of drug. The material can be compressed in aluminum or stainless steel molds situated in a Carver hydraulic press at 12 tons of pressure for at least 15 minutes at 100 degrees C.

As a further example, the device may be formed of methacrylate hydrogels prepared as follows:

Hydrogels loaded with drug can be constructed from crosslinked methacrylate polymers which include compositions containing one or more of the following: 2-hydroxyethyl methacrylate (HEMA), ethylene glycol dimethacrylate, polymethylmethacrylate, methylmethacrylate, glycol monomethacrylate, ethylene monomethacrylates, glycol dimethacrylates, vinylpyrrolidone, methacrylic acid, divinylbenzene, and alkyldiol methacrylates, acrylamide, methylene bis acrylamide.

Various crosslinking percentages can be achieved by altering the ratios of the copolymers. For example a 40:1 weight ratio of acrylamide to methylene bis acrylamide produces a 2.5% crosslinking. A buffered solution (pH 7–9) of the copolymers is made containing the desired crosslinking ratio. The final total polymer percentage can be varied from 1 to 25%. Drug is admixed into this solution. Suitable crosslinking free radical generator and catalyst (such as ammonium persulfate and tetra methyl ethylene diamine) is added. The mixture is poured into an appropriate mold with the desired shape. Polymerization occurs within 30 minutes.

These embodiments of the invention may employ the ophthalmic drugs and pharmaceutically acceptable carriers as previously described.

The following are specific examples which were carried out in accordance with the present invention.

EXAMPLE 1

One part of silastic MDX4-4210 curing agent (Dow Corning Corp, Midland, MI) was mixed with 10 parts of MDX4-4210 Silastic base elastomer (Dow Corning Corp, Midland, MI). The material was placed under a vacuum of about 28 inches of mercury for 30 minutes. Material was then transfered into a cylinder situated in a transfer press. The material was then forced into a 12 cavity aluminum mold heated to 135 degrees C. which contained impressions of the ribbed device design and forced into the mold at a transfer pressure of 400 psi for 3.5 minutes. The mold itself is kept under 10 tons of clamp pressure. The mold was cooled, separated and the formed devices were removed. The devices were cleaned by soaking in isopropyl alcohol for approximately 5 minutes and allowed to air dry.

EXAMPLE 2

One part of silastic MDX4-4210 curing agent (Dow Corning Corp, Midland, MI) was mixed with 10 parts of MDX4-4210 silastic base elastomer (Dow Corning Corp, Midland, MI). Oxytetracycline hydrochloride (Sigma Chemical Co., St. Louis) in the amount of 1% by weight of the total mixture was thoroughly blended in with care taken to minimize entrapment of air. The material was placed under vacuum of about 28 inches of mercury for 30 minutes. Material was then transfered into a cylinder situated in a transfer press. The material was then forced into a 12 cavity aluminum mold heated to 135 degrees C. which contained impressions of the ribbed device design and forced into the mold at a transfer pressure of 400 psi. The mold itself was kept under 10 tons of clamp pressure for 3.5 minutes. The mold was cooled, separated and the formed devices were removed.

EXAMPLE 3

One part of Silastic MDX4-4210 curing agent (Dow Corning Corp, Midland, MI) was mixed with 10 parts of MDX4-4210 Silastic base elastomer (Dow Corning Corp, Midland, MI). Oxytetracycline hydrochloride (Sigma Chemical Co., St. Louis) in the amount of 20% by weight of the total mixture was thoroughly blended in with care taken to minimize entrapment of air. The material was placed under vacuum of about 28 inches of mercury for 30 minutes. Material was then transfered into a cylinder situated in a transfer press. The material was then forced into a 12 cavity aluminum mold heated to 121 degrees C. which contained impressions of the ribbed device design and forced into the mold at a transfer pressure of 800 psi. The mold itself was kept under 10 tons of clamp pressure for 3.25 minutes. The mold was cooled, separated and the formed devices were removed.

EXAMPLE 4

Silastic medical grade ETR elastomer Q7-4720 (Dow Corning Corp, Midland, MI) was prepared by first individually softening Part B and Part A of the elastomer on a cooled two-roll mill. The two components were then blended together in a 1:1 ratio on the two-roll mill. Material was then transfered into a cylinder situated in a transfer press. The material was then forced into a 12 cavity aluminum mold heated to 121 degrees C. at a transfer pressure of 800 psi. The mold itself was kept under 10 tons of clamp pressure for 3.25 minutes. The mold was cooled, separated and the formed devices were removed.

EXAMPLE 5

Medical grade liquid silicone rubber Silastic Q7-4840 A/B (Dow Corning Corp, Midland, MI) was prepared by mixing equal portions of the A and B components. A vacuum of 29–29 inches of mercury was applied to the mixture for 30 minutes to deair the material. The material was compression molded in an aluminum mold in a carver press for 15 minutes at 100 degrees C. under 12 tons of pressure. The mold was cooled, separated, and the devices removed. The devices were cleaned by soaking in isopropyl alcohol for approximately 5 minutes and allowed to air dry.

EXAMPLE 6

Silastic medical grade ETR elastomer LSR 76000 (Dow Corning Corp., Midland, MI) was prepared by first individually softening Part B and Part A of the elastomer on a cooled two-roll mill. The two components were then blended together in a 1:1 ratio on the two-roll mill. Oxytetracycline hydrochloride with or without USP grade dextrose premixed in various ratios was added incrementally into the blend to assure homogeneous distribution. Material was then transferred into a cylinder situated in a transfer press. The material was then forced into a 12 cavity aluminum mold heated to 121° C. at a transfer pressure of 800 psi. The mold itself was kept under 10 tons of clamp pressure for 3.25 minutes. The mold was cooled, separated and the formed devices were removed.

EXAMPLE 7

For control devices not containing any protrusion beyond the core, simple cylindrical rods were prepared as in Example 1 except using a mold with impressions of a simple rod shape.

EXAMPLE 8

A study was carried out in which the device of the present invention was inserted into the eyes of human patients with either no disease or suffering from conjunctivitis, corneal disease, anterior uveitis, trachoma, or episcleritis. Initially, one drop of anesthetic was placed on the eye. After 2 minutes a small amount of eye ointment (such as Neosporin, Burroughs Wellcome, Research Triangle Park, NC) was applied to the lower fornix. The subject was instructed to blink several times. After two to three minutes either the ribbed device of Example 1 or non-modified rod controls of Examples 2, 5 or 7 were secured in the middle with a clean blunt forceps. With the subject looking down, the upper lid was separated from the globe using the thumb of the free hand. With the subject continuing to look down, the tip of the forceps and the device was gently pushed under the lid toward the fornix about 6-7 mm inward, making sure the device was centered in the fornix. The device was released from the forceps. With a tip of the finger the device was maneuvered into the deep fornix. The subject was instructed to move the eye up and down 3 times while holding the tip of the finger over the lid near the fornix. Results are shown below in Table 1.

TABLE 1

| Device Type | Days Retained in Fornix | Number (percent) of patients retaining device |
|---|---|---|
| Control devices without ribbing (from Examples 4, 5, and 7) | 0-6 | 36 (40.5%) |
|  | 7-28 | 53 (59.5%) |
| TOTAL |  | 89 (100%) |
| Ribbed devices (from Example 1) | 0-6 | 3 (20%) |
|  | 7-28 | 12 (80%) |
| TOTAL |  | 15 (100%) |

Conclusion: In these experiments ribbed OCUFIT SR devices minimized lateral movement and are better retained in the fornix (80%) than rods without ribbing (59.5%) in ocular disease patients for periods of 7-28 days.

Additional work was carried out to study the retainability of a ribbed OCUFIT SR device measuring 25 mm in length ×1.4 mm (core diameter) and 1.7 mm (protrusion diameter) for a period of up to four weeks in the normal eyes of human volunteers. These were patients whose eyes were free of active disease as compared to the study of Example 8 above in which most of the patients were suffering from eye disease at the time of the test.

The configuration of the ribbed OCUFIT SR device was as shown in FIG. 7 of the drawings but with five ribs. The material employed was a solid silastic based material MDX4-4210, a medical grade elastomer. No drug was incorporated into the OCUFIT SR device and the ends of the device were rounded.

This additional study was carried out in the eyes of human volunteers, rather than experimental animals since the size and depths of the upper or lower fornix of experimental animals are different from the human eye. In some animals, the presence and movement of nictitating membrane can dislodge the OCUFIT SR device.

The method used in this study was as follows:

The volunteer was asked to sit down, hold his/her chin slightly up and to look down continuously throughout the exercise.

The eye was anaesthetized by a drop of Benoxenate (oxybuprocaine) hydrochloride 0.4% W/V (Smith & Nephew).

The upper lid was separated from the globe by about 4 to 5 millimeters by holding lashes and gently pulling the lid backward and upward. The OCUFIT SR device held in the forceps was centrally located at a midpoint between the nasal and temporal canthus and was pushed under the upper lid inward about 6 to 7 mm. The tip of a finger was positioned in the middle of the eyelid just above the end of the forceps before the OCUFIT SR device was released and forceps removed. The device was released and the ends of the device were allowed to orient toward the respective canthus. With the tip of a finger the OCUFIT SR device was gently pushed upward and toward the deep fornix. The maneuver was repeated twice more in each corner (canthus). The volunteer was asked to move the eye downward and upward three times.

The volunteer was advised:

(a) If he/she feels that the end of the OCUFIT SR device was near the inner or outer corner (nasal or temporal canthus) of the eye or feels irritation, he/she can push the OCUFIT SR device back to the middle of the fornix by closing the eye and looking down, then, with the tip of a finger gently press the corner of the eye.

(b) Repeat maneuver explained above once in the morning after waking up and once in the evening before sleeping.

(c) Avoid rubbing the eyes.

(d) It is not possible to visualize the OCUFIT SR device in the deep fornix but he/she may be aware of sensation in a corner of the eye, relieved by prodding the upper part of the lid with a finger tip after closing the eye.

After taking a history, the eyes were examined by a slit lamp. The clinical signs of the conjunctiva, cornea and anterior urea were recorded on a specially designed proforma.

The duration of retention was planned for four weeks.

Alternatively, a mechanical insertion device may be employed for insertion of the device of the present invention.

No additional topical or systemic treatment was given to any of the volunteers. The volunteers were asked to report to the investigator if the OCUFIT SR device was rejected from the eye.

The results of the retention study are shown in Table 2.

TABLE 2

| | | | | | | | | | | | |
|---|---|---|---|---|---|---|---|---|---|---|---|
| RETENTION OF RIBBED OCUFIT SR DEVICE IN THE EYE OF VOLUNTEERS | | | | | | | | | | | |
| Sub. No. | Initial | Age | Sex | Eye | \multicolumn{6}{c}{Days of Retention} | | | | | OCUFIT SR |

| Sub. No. | Initial | Age | Sex | Eye | 1 | 5 | 11 | 24 | 28 | 32+ | OCUFIT SR |
|---|---|---|---|---|---|---|---|---|---|---|---|
| 1 | MMR | 29 | F | N |  |  | 11 |  |  |  | Rej. |
|  | MMR** | 29 | F | N |  |  |  |  |  | 32 | Rem. |
| 2 | AH | 24 | F | N | 3 |  |  |  |  |  | Rej. |
| 3 | SD | 63 | M | N |  |  |  |  |  | 64 | Rem. |
| 4 | MH | 25 | M | N | 5 |  |  |  |  |  | Rej. |
| 5 | JH | 22 | M | N |  |  |  |  | 28 |  | Rem. |
| 6 | AG | 23 | M | N |  |  |  |  | 28 |  | Rem. |
| 7 | MG | 24 | M | N |  |  |  | 24 |  |  | Rej. |
| 8 | SH | 22 | M | N |  |  |  |  | 28 |  | Rem. |

TABLE 2-continued

RETENTION OF RIBBED OCUFIT SR DEVICE IN THE EYE OF VOLUNTEERS

| Sub. No. | Initial | Age | Sex | Eye | Days of Retention | | | | | OCUFIT SR |
|---|---|---|---|---|---|---|---|---|---|---|
| | | | | | 1 | 5 | 11 | 24 | 28 | 32+ | |
| 9 | RMW | 43 | M | N | - - - - - 5 | | | | | | Rej. |

N = Normal
** = Second attempt
Rej. - Rejected
Rem. - Removed

Nine volunteers with normal eyes were included. The age and gender of the volunteers are presented in Table 2.

In eight volunteers, the OCUFIT SR device was inserted once and in one volunteer (MMR) it was inserted twice.

The OCUFIT SR device was inserted in the upper fornix of the left eye in 8 volunteers and in the upper fornix of the right eye in one volunteer (RMW).

The period of retention for each volunteer is shown in Table 2. In six volunteers (67%), the OCUFIT SR device was retained for 24 days or more. Of these, five retained the device for 28 days or longer before it was removed and in one volunteer (case 7, MG) the OCUFIT SR device came out on day 24 for no apparent reason. In one volunteer (case 1, MMR) the first OCUFIT SR device came out on day 11 after vigorous physical exercise. The second OCUFIT SR device in this volunteer retained well for 32 days before it was removed. In three volunteers (cases 2,4 and 9) the OCUFIT SR device retained between 3 and 5 days respectively. In cases 2 and 4, OCUFIT SR device was rejected after rubbing of the eye and in case 9, it came out from the outer corner of the eye for no apparent reason.

Figure 13:
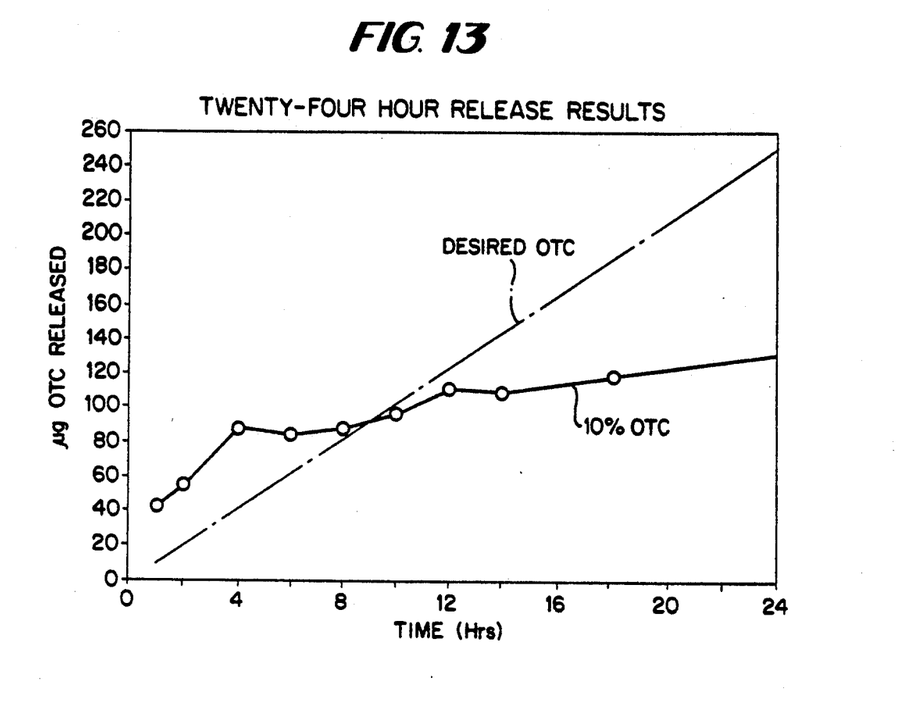
FIGS. 13 through 16 are graphic representations showing data in regard to drug release and swelling rate in accordance with the present invention.
Figure 14:
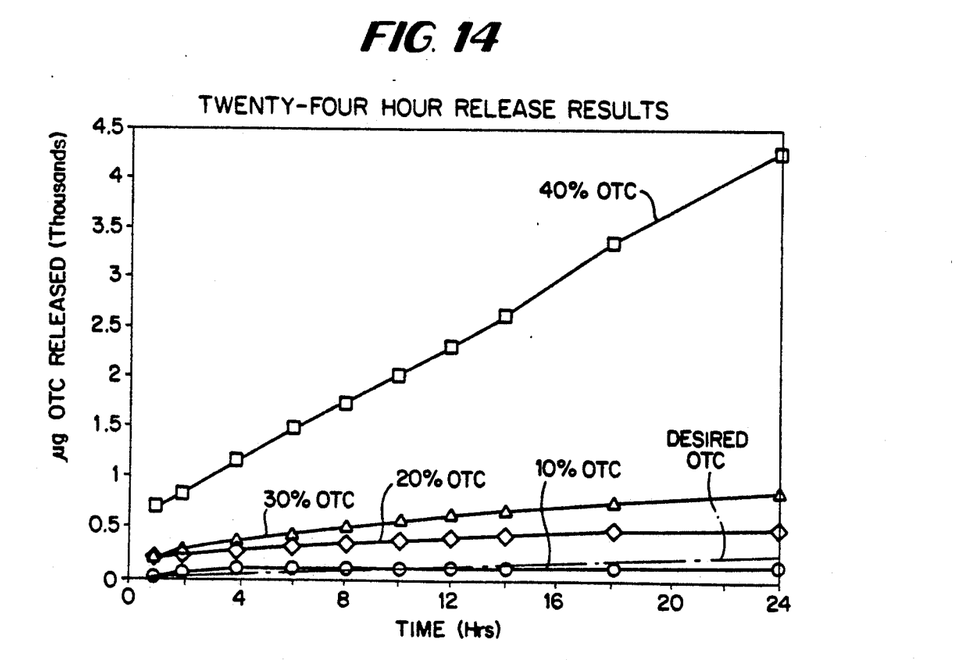

In FIGS. 13 and 14, there are provided various graphs showing drug release data in accordance with the present invention. In FIG. 13 a Q7-4735 elastomer was employed and the desired or theoretical release rate for efficacy is shown as well as results obtained when the device was loaded with oxytetracycline in an amount of 10% of the weight of the unloaded device.

The data in FIG. 14 is for various amounts of loading of oxytetracycline in a device formed of the MDX4-4210 elastomer, with FIG. 14 showing results over a 24 hour period.

Figure 15:
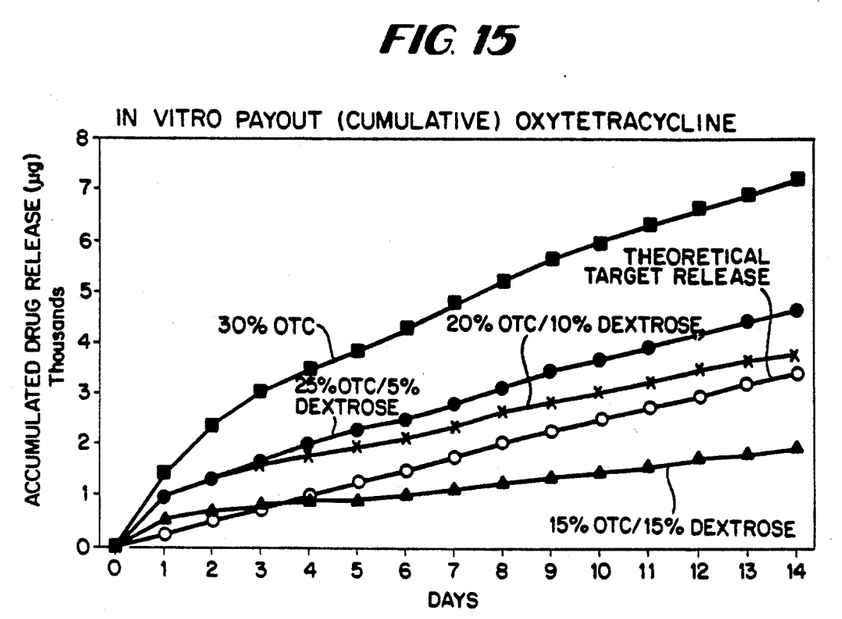

FIG. 15 shows a graph of drug release data in accordance with the present invention, in which dextrose is employed as a release modifier. As shown in the graph, the solids percentage is maintained at 30% and the amount of dextrose is varied between 0 and 15%, as shown in the different curves. By adding dextrose, more pores or pathways are created for drug diffusion. These drugs are employed with suitable carriers as previously discussed.

Figure 16:
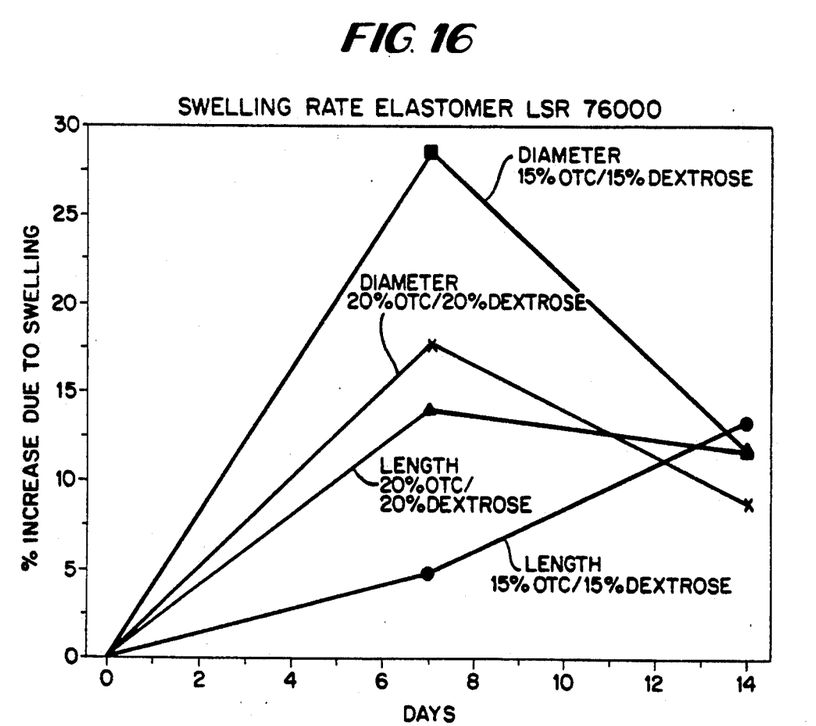

In FIG. 16 there is shown a graph of the swelling rate of a particular elastomer employed in a device of the present invention. Swelling is caused by the migration of water into the polymer, dissolving the drug and causing the polymer to swell due to an osmotic effect as water forces the polymer outwardly. Such swelling can be desirable inasmuch as a device of the present invention may lock into place as it grows in size. It has been found that the silicone materials are particularly prone to swell in this manner. As indicated by the graph, it is within the scope of the invention to select the initial dimensions of a device and, by selecting the proper combination of solid materials, e.g., oxytetracycline and dextrose, to provide for the desired final dimensions of the device after swelling.

In FIG. 16 there are shown the measurements obtained with regard to swelling of a device of the present invention which has been loaded with oxytetracycline and dextrose. At large drug loads, the device can swell so that both length and diameter are increased significantly. In view of this tendency to swell when drug has been incorporated, there are several possible approaches: (1) start with a small rod that is initially inserted; (2) adjust the ratio of drug to release modifiers which will affect the rate of water diffusion into the rod; and (3) adjust the amount of platinum catalyst to facilitate more complete cross-linking of the polymeric rod material which reduces the amount of swelling.

The data in Table 3 show physical properties, including tensile strength and % elongation for a device of the present invention prepared in various formulations with various amounts of oxytetracycline, glycerine and polyethylene glycol.

TABLE 3

| | PHYSICAL PROPERTIES | |
|---|---|---|
| FORMULATION | TENSILE (PSI) | ELONGATION (%) |
| 30% OTC | 287.2 | 622.8 |
| 10% OTC; 5% GLY | 382.5 | 604.6 |
| 30% OTC; 10% PEG 8000 | 183.5 | 534.6 |

While the ocular insert of the present invention has been described herein as particularly well suited for treatment of humans, it is also within the scope of the invention to employ the present invention in the treatment of other animals such as cows and horses for diseases such as pink eye and the like.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for the controlled sustained release of an ophthalmic drug into the eye over a period of time which comprises:
   (a) inserting an elongated device having a body of polymeric material in the form of a rod or tube containing an ophthalmic drug into the upper or lower fornix so as to anchor said device into position therein, with at least two anchoring protrusions extending radially outwardly from said body, said device having a length of at least 8 mm and a diameter including protrusions which does not exceed 1.9 mm, wherein said device is sufficiently flexible to allow it to bend along the curvature of the eye within the upper or lower fornix upon being position so that the longitudinal axis of said device is generally parallel to the transverse diameter of the eyeball, said device being of a size and configuration such that, upon insertion into the upper or lower fornix, the device does not extend onto any visible portion of the eyeball, said device being independent of movement of the eye and remaining out of the field of vision so as to be well retained in place and imperceptible by a patient over a prolonged period of use, with said protrusions acting to minimize lateral movement of the device within the fornix; and (b) allowing said device to remain in the upper or lower fornix for drug release during said period of time, whereby the device when inserted into the upper or lower fornix can be retained therein for more than seven days.

2. The method of claim 1 wherein the protrusions extend outwardly a distance such that the overall diameter of the device including the protrusions is approximately 15 to 30 percent greater than the diameter of the body of said device.

3. The method of claim 1 wherein said protrusions are evenly spaced relative to the length of the device.

4. The method of claim 1 wherein said protrusions are positioned so as to be symmetrical with respect to said body.

5. The method of claim 1 wherein said protrusions are toroidal or doughnut shaped around the body to provide a ribbed configuration.

6. The method of claim 1 wherein said protrusions are in the form of a winding such as a screw thread around the body.

7. The method of claim 1 wherein said protrusions are in the shape of hemispherical dimples or bumps.

8. The method of claim 1 wherein said protrusions are in the form of a series of truncated cone-shaped segments wherein the longitudinal axis of said cone-shaped segments is coaxial with the longitudinal axis of said body.

9. The method of claim 1 wherein said truncated cone-shaped segments are arranged so that a portion of said device is a mirror image of another portion of said device.

10. The method of claim 1 wherein said protrusions are in the form of winding braid segments.

11. The method of claim 1 wherein the length of the device is from 8 to 25 mm for use in the lower fornix to suit the eyes of different sizes such as infants, children And adults.

12. The method of claim 1 wherein the length of the device is from 8 to 35 mm for use in the upper fornix to suit the eyes of different sizes such as infants, children and adults.

13. The method of claim 1 wherein the diameter of the device including protrusions is from 0.5 to 1.9 mm to suit the eyes of different sizes such as infants, children and adults.

14. The method of claim 1 wherein the body is tubular and the mechanism of drug release is by diffusion through an outer wall of the device.

15. The method of claim 1 wherein the body is tubular and the mechanism of drug release is by osmosis.

16. The method of claim 1 wherein the body is in the shape of a rod and the mechanism of drug release is bioerosion.

17. The method of claim 1 wherein the body is a non-erodible rod and the mechanism of drug release is by diffusion including possible drug dissolution.

18. The method of claim 1 wherein said device has a cylindrical shaped body.

19. The method of claim 1 wherein said device has a polygonal shaped body.

20. The method of claim 1 wherein insertion of the device is accomplished by (a) securing the device centrally with respect to the nasal and temporal canthus, (b) gently inserting the device under the lid at a midpoint between the nasal and temporal canthus and from 6 to 7 mm inward while the lid has been separated from the globe by about 4 to 5 mm, (c) releasing the device and allowing the ends to orient toward the respective canthus, and (d) using the tip of the finger on the surface of the lid to manipulate the device into final position in the deep fornix.

21. The method of claim 1 which further includes selecting as the polymeric material for the body a material which is subject to swelling in a liquid environment.

22. The method of claim 21 wherein a device is employed having dimensions which initially are smaller than the desired final dimensions, so that the device is assisted in locking into place as the device increases in size after insertion into the fornix.

23. The method of claim 21 which includes the further step of adjusting the ratio of drug to release modifier during manufacture of said device to affect the rate of liquid diffusion into the device.

24. The method of claim 21 which includes the further step of adjusting the amount of catalyst during manufacture of said device to facilitate the amount of cross-linking and thus the amount of swelling of the polymeric rod material.

25. The method of claim 21 wherein the device increases in size in both length and diameter.

* * * * *